United States Patent [19]

Teinturier

[11] Patent Number: 5,041,140
[45] Date of Patent: Aug. 20, 1991

[54] REPLACEMENT JOINT PROSTHESIS

[76] Inventor: Pierre Teinturier, Champeaux, 63122 Ceyrat, France

[21] Appl. No.: 242,107

[22] Filed: Sep. 8, 1988

[30] Foreign Application Priority Data

Sep. 8, 1987 [FR] France .................... 87 12428

[51] Int. Cl.⁵ .............................................. A61F 2/32
[52] U.S. Cl. .......................................... 623/22; 623/23
[58] Field of Search ................. 623/16, 18, 20, 22, 623/23

[56] References Cited

FOREIGN PATENT DOCUMENTS 0144588 6/1985 European Pat. Off. ............. 623/23
2483218 12/1981 France .................................. 623/22

*Primary Examiner*—David J. Isabella
*Attorney, Agent, or Firm*—Larson and Taylor

[57] ABSTRACT

A hip joint prosthesis comprises a femoral unit and an acetabulum unit. The acetabulum unit has a rigid cap of a material having a low coefficient of friction, defining a cavity which receives the ball head of the femoral unit, and an outer shell having a rigid radially inner part accommodating the cap and a resilient radially outer part anchored in the pelvic bone and radially deformable. For imparting resiliency to the outer part, it may be fractionated into a plurality of finger-like angular sectors each joined to the inner part by an annular zone of reduced thickness. The femoral unit may also be rendered resilient, for instance by locating a plurality of corrugated rings in recesses distributed along the length of its shaft.

13 Claims, 3 Drawing Sheets

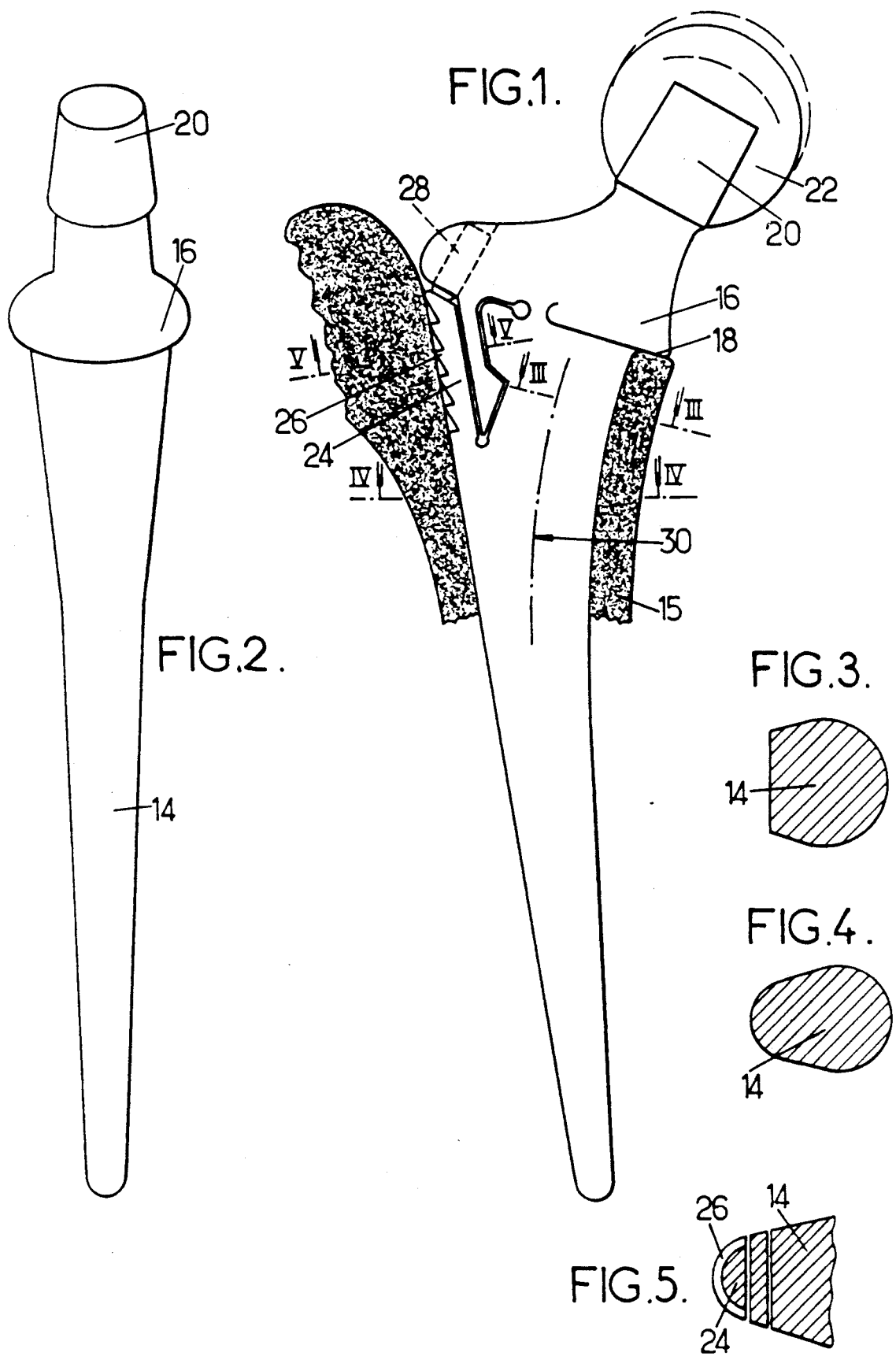

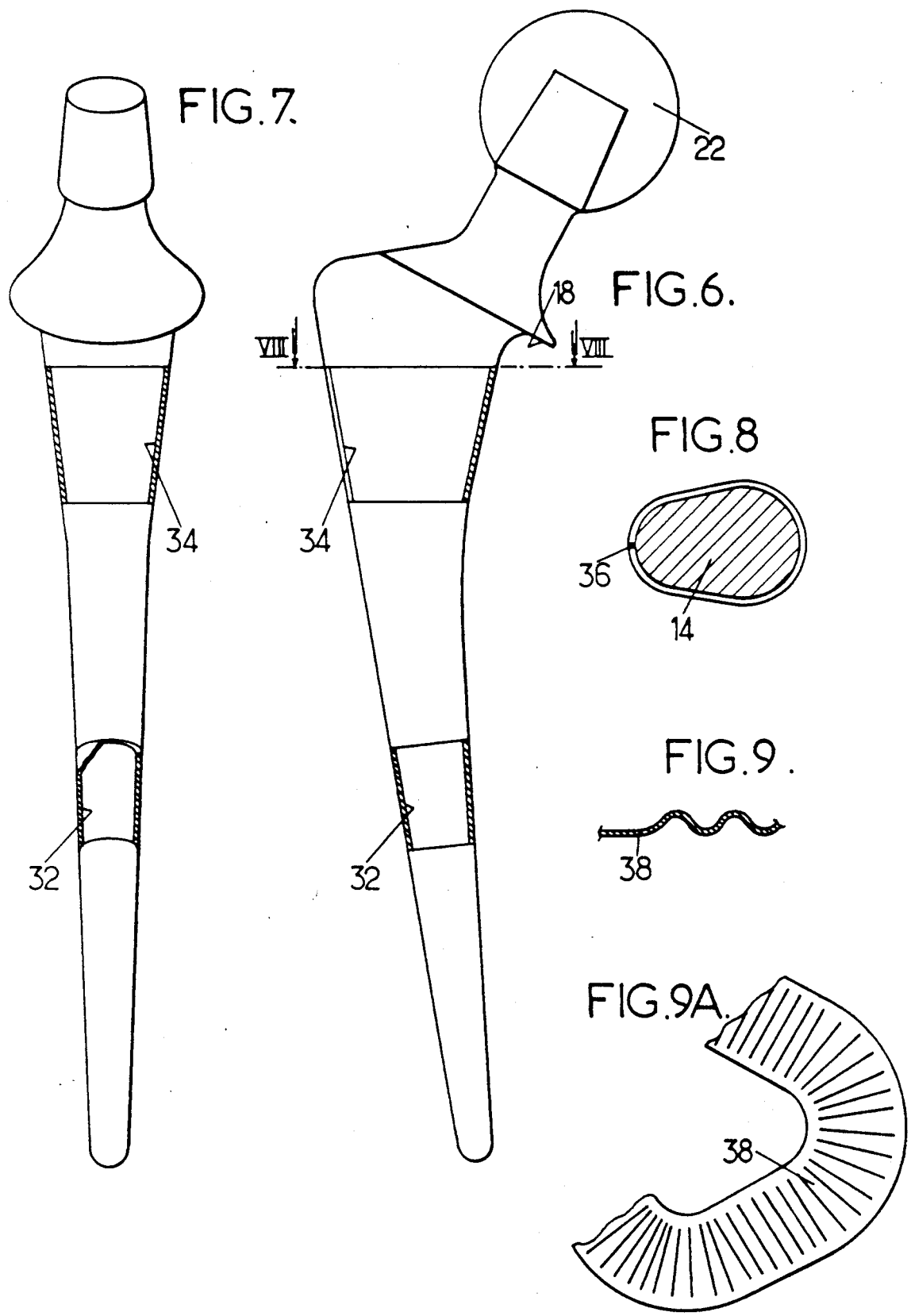

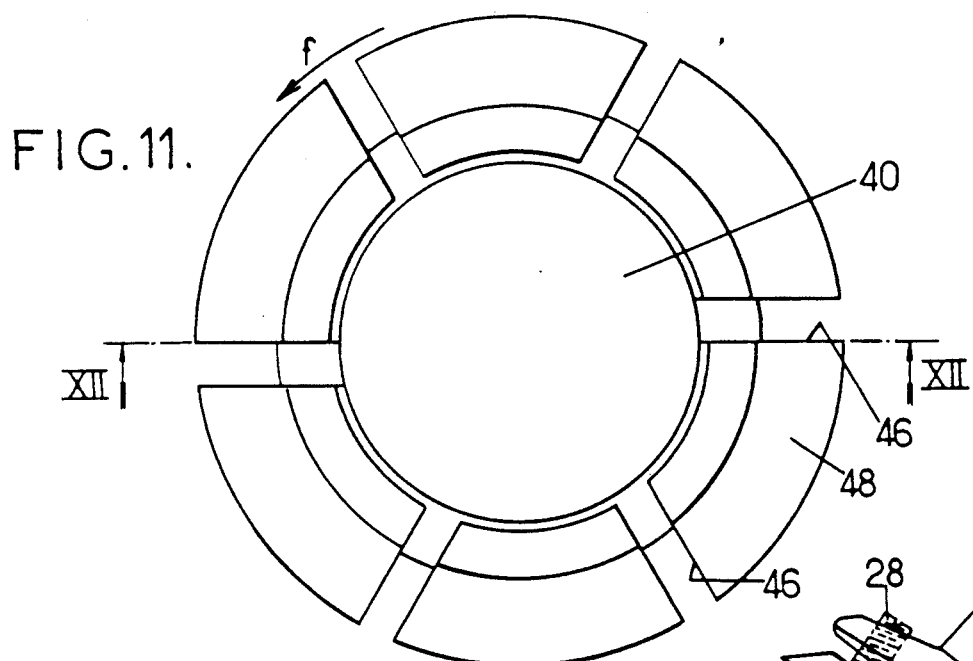
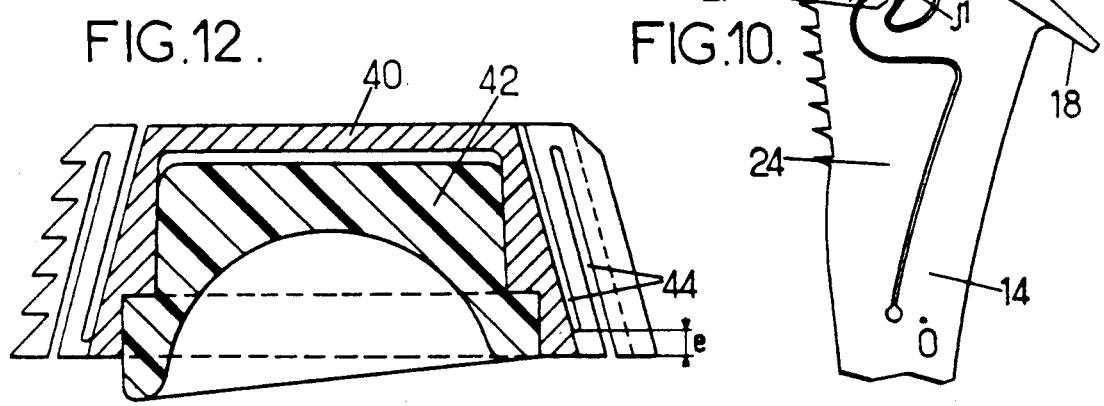
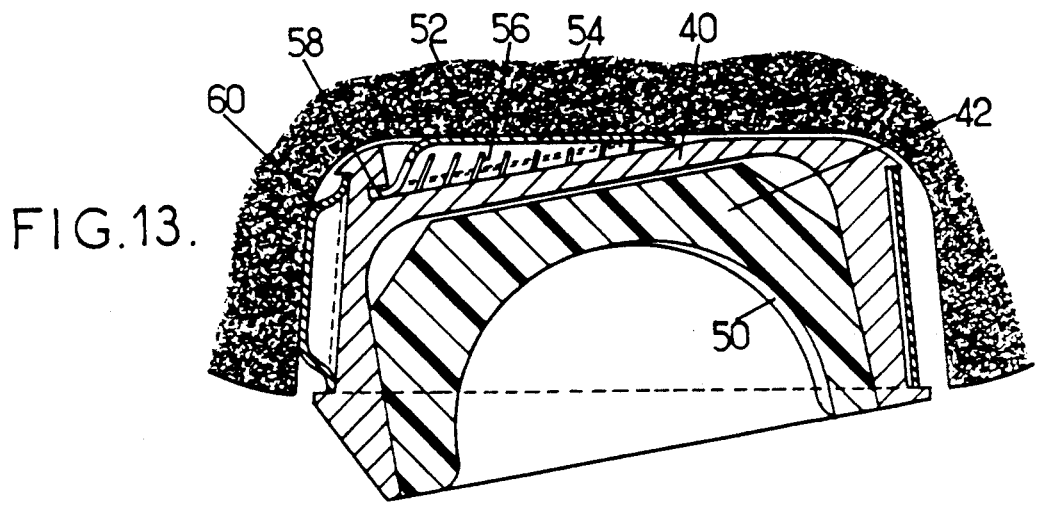

REPLACEMENT JOINT PROSTHESIS

BACKGROUND OF THE INVENTION

1. Technical Field

The invention relates to replacement joint prostheses of the type comprising two parts designed to be anchored in complementary elements of the skeleton and having surfaces for mutual sliding or rolling movement simulating the movements of a natural joint as exactly as possible.

It is particularly, although not exclusively, suitable for use in the field of hip joint prostheses, which are at the present time those most frequently implanted and are particularly well adapted to implementation of the invention. It is however not limited to this particular case and it is equally applicable to prostheses of the knee (which, like those of the hip, have to support the weight of the patient during walking).

2. Prior Art

For a long time it has been postulated that it is necessary to secure rigidly, by cementing, one at least of the parts of the prosthesis. In the case, for example, of the prosthesis of the hip, most of existing prostheses comprise a solid femoral part designed to be anchored mechanically or by cementing in the medullary channel of the femur and an acetabulum unit in the form of a cup designed to be tightly received in a cavity formed in the pelvic bone. Whether the cup is locked by cementing or by screwing or whether it is left free to slide if the two parts come into mutual abutment due to an excess rotation, the prosthesis cannot follow the deformations of the skeleton under load.

An attempt has recently been made to take into account the deformations of the femur under load by imparting some degree of flexure elasticity to the shaft of the femoral part of a hip joint prosthesis. Such construction only contributes a partial and incomplete solution to the problem.

SUMMARY OF THE INVENTION

A priori, it could be thought that imparting to the constituent parts of a prosthesis an elasticity enabling them to adapt themselves to the deformations of the skeleton is to be excluded, since the deformations could interfere with, or even block the mutual movements required for the freedom of the joint. It is an object of the invention to provide an improved prosthesis of the above-defined type enabling the required compliance to be obtained without detrimentally affecting movement, by uncoupling the functions of adaptation to the deformations of the skeleton and of an invariable geometry of the contact surfaces.

With this object in mind, there is provided a prosthesis of which the two parts have mutual sliding or rolling surfaces formed in undeformable portions one at least of which is supported by the respective bone through means which are elastically deformable to some extent.

Frequently, one of the parts of the prosthesis is arranged to have an intramedullary fixation channeling the stresses received by the prosthesis. This is for example the femoral part in a hip joint. The resulting lack of load of the cortex in conventional prostheses introduces a risk of bone atrophy. According to one aspect of the invention, atrophy is avoided by means for transmitting loads to the cortex. According to an embodiment of the invention, the intramedullary portion of the part is covered with deformable means (such as an expansion ring) over a length selected according to the nature of the prosthesis and the length of the intramedullary shaft. In another embodiment, possibly used in conjunction with the first, there is provided deformable means arranged to apply an axial force for loading the cortices beneath an enlargement of a collar-forming section in contact with the bone section. Yet another solution consists of machining a forged blank which is slightly larger than its housing in the medullary channel by cutting out, possibly by electro-erosion, slots defining several portions in the shaft which remain connected to preserve proximal and distal hinges. In this manner, a resilient support is obtained.

Very often also, the second part of a prosthesis is designed to be forced into a cavity cut in a cotyle. In the particular and typical case of a hip joint prosthesis, comprising an acetabulum unit defining a housing in the form of a spherical cap and a femoral part terminated by a ball head, it is particularly important that the acetabulum unit be able to follow bone deformations under load and adapt thereto. For this, the acetabulum unit may have various constructions. The part may comprise an inner rigid cap of a material having a low coefficient of friction and a high wear resistance, of a conventional type, contained in a shell whose outer zone is radially resiliently deformable. The outer zone may be integral with an inner zone and constitute a liner divided into several sectors by radial slots and/or jointed to the central portion by a ligament defined by a circumferential groove. Several grooves positioned in staggered relationship in the radial direction may be provided to constitute a multiple liner increasing flexibility.

When this solution is adopted, it is possible to introduce the acetabulum unit into a previously prepared cavity having a size slightly lesser than that of the implanted shell, which will be anchored in place by elastic expansion pressure. It is also possible to form an external screw thread with edges of dissymetric shape for screwing the part, thereby preserving a method of fixation widely used in current hip joint prosthesis.

In another embodiment, the shell is of composite construction: it has a rigid metal body and resilient means bonded to the body to exert pressure in the radial and/or axial direction. The covering means may envelope the body over part only of its external surface area.

Still other embodiments are possible: the shell may comprise a rigid inner shell and a deformable outer shell defining an intermediate closed cavity filled with a damping and deformation absorbing material for distributing the stresses, for example a very viscous liquid or pasty material.

The invention will be better understood from a consideration of the following description of particular embodiments, given by way of examples only. The description refers to the drawings.

BRIEF DESCRIPTION OF THE DRAWINGS

FIG. 1 is a view in elevation and in partial cross-section of a femoral part of a hip joint prosthesis according to a particular embodiment of the invention;

FIG. 2 is a view from the right of FIG. 1;

FIGS. 3, 4 and 5 are views in cross-section along lines III, IV and V of FIG. 1, respectively;

FIGS. 6 and 7, similar to FIGS. 1 and 2, show a modified embodiment;

FIG. 8 is a view in cross-section along line VIII—VIII of FIG. 6;

FIGS. 9 and 9A are detailed views showing respectively a fragment of a compliance ring for use on a shaft of the femoral part of FIGS. 6 and 7 and the general shape of a compliance ring, in developed view;

FIG. 10, similar to a fraction of FIG. 1, shows another modification;

FIGS. 11 and 12 show, respectively in view from above and in section along line XII—XII of FIG. 11, an embodiment of the acetabulum unit for a prosthesis according to the invention;

FIG. 13, similar to FIG. 12, shows a modified embodiment of the acetabulum unit.

DETAILED DESCRIPTION OF PREFERRED EMBODIMENTS

A hip joint prosthesis according to the invention can comprise a femoral part according to one of the embodiments shown in FIGS. 1 to 10 and/or an acetabulum unit according to one of the embodiments shown in FIGS. 11 and 13, or modifications thereof.

Referring to FIGS. 1 to 6, a femoral part consists of a solid metal part of a metal or alloy compatible with organic tissues. It is possible particularly to use titanium-base alloys (such as alloy UTA 6V), several stainless steels and the alloy know under the trade name "VITALLOY". The part is obtained by machining a forged or stamped blank; it may be regarded as having a shaft 14 for anchoring in the medullary channel of the femur 15, of tapered shape from the bottom end, a collar 16 having a lower shoulder 18 for cortical support and a tapered end pin 20 for receiving a ball head 22 (FIG. 1), of hard material with a low coefficient of friction, in the shape of a spherical cap whose diameter is generally comprised between 22 and 32 mm. The taper of the pin maY be so chosen that a self-holding friction fit is formed between the pin and the cap.

For easier adaptation of the prosthesis to the anatomy of various patients, several ball heads are generally provided which differ from one another in respect of the emplacement of the tapered pin and/or the diameter of the spherical cap, enabling the frictional surface to be given different locations with respect to the cortical support, as indicated by dashed lines in FIG. 1.

To provide anchoring without cementing of the femoral part and permanent axial load of the cortical portions of the bone, the upper portion of the femoral shaft 14 is cut out to define a resiliently flexible finger 24 formed with an anchoring rack 26 (FIGS. 1 and 5). The cut-out slot has such a length as to define, in the main portion of the shaft which is joined to the collar 16, a cross-section where the stress is maximum, as indicated by line III—III in FIG. 1. To reduce the thickness of the cut-out slot to a minimum, cutting out may be performed by electro-erosion with a wire. An enlargement is provided at the end of the cut-out slot and in a sharp corner of the latter to avoid stresses which could lead to cracking.

In the bulged collar 16 an internally threaded hole is formed for receiving a pressure screw 28 arranged to abut the end of finger 24 and to force the latter in a direction causing it to flex away from the main portion of the shaft. This pressure screw enables at the same time to anchor the rack 26 into the medullary wall and to impress an axial load on the cortex. For insertion of the femoral part, the screw 28 is untightened. The resiliency of finger 24 biases it towards the neutral line 30 of the part. The femoral part is inserted into the medullary channel after preparation of the femur and particularly cutting out of the support surface of the shoulder 18. Then the screw is tightened.

In the embodiment shown in FIGS. 6 to 9A (where elements corresponding to those of FIGS. 1 to 5 are denoted by the same reference numeral), the femoral part is solid and not cut-out. On the other hand, it has shallow slightly frustoconical grooves 32 and 34 for receiving compliance rings (not shown in FIG. 8). The groove 32, placed a little below the half-length of the shaft of the part, has a length comprised between 15 and 25 mm (20 mm for example). The groove 34 placed immediately beneath the shoulder 18 for abutting connection with the femur has a greater length, usually between 20 and 30 mm (25 mm for example).

The two compliance rings are resiliently radially expandable. They have the same general construction. Their function is to maintain the femoral part within the bone whilst compensating for the deformations of the bone which lead to modification of the distance between the axis of the shaft and the wall of the medullary channel. They may be of the same material as the femoral part and in the form of a folded band whose ends are separated by a gap placed in the middle plane of the outer side of the shaft, that is at 36 on FIG. 8. Each compliance ring may have a corrugated shape, the orientation of the undulations being as shown in FIG. 9A. Such a ring 38 may for example, when provided to be placed in a groove of 0.8 to 1.2 mm depth, have a thickness of some tenths of a millimeter with an undulation spacing of 2 to 3 mm and a wave depth greater by some tenths of a millimeter than the depth (typically 2/10 mm approximately).

Other embodiments of the rings may be used, for example having cut-out tabs bent alternately to one side and the other of the ring.

In the modification shown in FIG. 10 (where elements corresponding to those of FIGS. 1 to 5 are again denoted by the same reference numeral), the upper portion of the femoral shaft 14 is again cut-out and defines an elastic finger 24 formed with a rack 26. The cutting out is more complex than in the case of FIG. 1 so that in the solid portion of the shaft there subsists a hook 27 constituting an abutment limiting the amount of flexure movement of finger 24.

The screw 28 for exerting a pressure force on the finger 24 is unscrewed for introduction of the femoral part until the collar 18 is in abutment on the cortex. Upon initial tightening of the screw 28, the finger 24 bends around point 0 in the solid portion, close to the end of the cut-out and moves away from the main part. The amount of flexure movement is limited by abutment of the finger against hook 27. Further tightening of the screw 28 results into a second bending movement, which takes place around a different point and tends to further apply the collar 18, thus ensuring a second pre-stressing. The amplitudes of the two successive flexion movements are limited to the values corresponding to the initial gaps j1 and j2 suitably selected.

The acetabulum unit shown in FIGS. 11 and 12 also has a construction enabling it to adapt to the deformations of the skeleton and to absorb them. The part shown in FIGS. 11 and 12 is for fixation by screwing into the acetabulum cavity; the screw thread could particularly be replaced by sharp points for locking against movement in two directions.

The metal shell 40 consists of a single part and has an inner portion which is not cut out and defines a shouldered slightly frusto-conical recess in which the cup 42, generally of plastics material, has a press fit; the cup is for receiving the ball head of the femoral part. Narrow frusto-conical circumferential grooves 44 (for example 0.5 mm wide) and radial slots 46 divide up the outer portion of the shell 40 into a series of resilient fingers 48 designed to absorb bone deformation.

It is possible to adjust the stiffness of the fingers, hence the force necessary for bending them, by suitably selecting the thickness of material which is left between the inner portion of the shell 40 and the fingers. A thickness e of about 2 mm will often provide satisfactory results, when the fingers themselves are about 1.5 mm thick. To increase resiliency, several circumferential cuts 44 may be arranged in quinqunx (two cuts in FIG. 12).

The outer surface of the fingers is self-threading with a pitch and a shape which can be conventional; for example, the pitch may be of 9 mm and the teeth may have a slope at 90° on one side, at 45° on the other. The rigid inner portion constitutes a housing for the cup 42. The outer portion constitutes a bonded liner, is fixed rigidly on the inner portion and may be similar in construction to that shown in FIGS. 11 and 12.

In the embodiment shown in FIG. 13, where the components corresponding to those of FIGS. 11 and 12 have again been denoted by the same reference numeral, the metal sheet 40 has a slightly frustoconical inner housing receiving the cup 42. The cup has one or a plurality of crescent shaped channels, for improving lubrication. The shell 42 rests on the bottom of a cavity formed in the bone 52 through resilient support means formed by a cup 54 of variable depth; the bottom of the cup abuts the bone and its edge is fractionated by slits 56 into tabs for support on the solid portion of the shell. To retain the cup on the shell, the tabs may have a folded lip 58 engaged in a groove formed at the bottom of a recess of the shell.

Radially the shell is supported on the bone through a resilient belt 60 of generally frusto-conical shape, having corrugations whose depth is greater than the distance between the lateral wall of the solid portion of the shell and the wall of the cavity formed in bone 52.

Still other embodiments are possible. For example, the shell may comprise two concentric shells, the inner shell being rigid and undeformable whilst the outer shell is deformable. A pressure transmitting medium is then placed in a chamber formed between the two shells.

The invention is in no way limited to the particular embodiments which have been illustrated and described by way of examples.

I claim:

1. Hip joint prosthesis, comprising:
    a femoral unit having an elongated anchoring shaft and a ball head; and
    an acetabulum unit having a rigid cap of a material having a low coefficient of friction, defining a cavity sized to slidably receive said ball head, and an outer shell including a rigid inner part configured to accommodate said cap, means for retaining said rigid cap in an invariable position with respect to said inner part and an outer part spaced apart from said inner part wherein said outer part is capable of being anchored in a pelvic bone of a patient and resiliently deformable radially toward and away from said inner part when said outer shell and rigid cap are in mutually assembled condition.

2. A hip joint prothesis according to claim 1, wherein said elongated anchoring shaft is cut out in an upper portion thereof for constituting a resilient finger formed with an anchoring rack on an outer surface thereof and wherein said femoral unit has an internally threaded hole opening at a position confronting said resilient finger and receiving a manually settable screw for forcing said finger apart from a neutral fiber of said shaft and anchoring the rack into the femoral bone of a patient.

3. Hip joint prosthesis comprising:
    a femoral unit having an elongated anchoring shaft and a ball head; and
    an acetabulum unit having:
    a rigid cap of a material having a low coefficient of friction, defining a cavity sized to slidably receive said ball head, and
    an outer shell including a rigid inner part accommodating said cap, retaining said rigid cap in an invariable position with respect to said inner part, and a resilient outer part capable of being anchored in a pelvic bone of a patient,
    wherein said outer part is integral with said inner part and said outer part is fractionated into a plurality of fingers by longitudinally directed slots about the circumference of the shell and said outer part is spaced apart, in a radial direction, from said inner part by a circumferential narrow groove.

4. Prosthesis according to claim 3, wherein said circumferential narrow groove is of frusto-conical shape.

5. Prosthesis according to claim 1, wherein said outer part is rigidly connected to said inner part along a circumferential zone over a fraction only of the length of said outer part.

6. Prosthesis according to claim 3, wherein said slots extend throughout said outer part.

7. Prosthesis according to claim 1, wherein said outer part consists of a liner of resiliently deformable material which at least partially covers said inner part to constitute a buffer between said inner part and the pelvic bone.

8. Prosthesis according to claim 7, wherein said inner part comprises a shell and wherein said liner consists of at least one of a metal resilient cup and a metal resilient belt carried by said shell constituting said inner part.

9. Prosthesis according to claim 1, wherein said inner part consists of a rigid shell and the outer part consists of a deformable shell which cooperates with the inner rigid shell to define a closed chamber accommodating a pressure distribution and transmission medium.

10. Prosthesis according to claim 3, wherein said anchoring shaft is of elongated shape for being received in a bone medular cavity and has recess means distributed along the direction of elongation and radially deformable members are received in said recess means.

11. Prosthesis according to claim 10, wherein said radially deformable resilient members consist of radially deformable corrugated rings arranged for filling a gap between a groove constituting said recess means and a femoral bone.

12. Prosthesis according to claim 1, having at least one additional circumferential narrow groove defining a zig-zag pattern with the first-named circumferential groove in any cross-section along a plane passing through an axis of said shell.

13. An acetabulum unit for a hip-joint prosthesis having a shell including:
    a rigid inner part defining a part-spherical cavity sized to slidably receive a ball head, and a resiliently deformable metal outer part capable of being mechanically anchored without cement in a pelvic bone of a patient, said outer part being fractionated into a plurality of fingers by longitudinally directed slots distributed along the circumference of the outer part, and said fingers being joined to said rigid inner part by an annular zone defined by at least one circumferential narrow groove allowing resilient deformation of said fingers.

* * * * *